US00PP11113P

United States Patent [19]

Yomo et al.

[11] Patent Number: Plant 11,113

[45] Date of Patent: Nov. 2, 1999

[54] VERBENA PLANT NAMED 'SUNMARIBISU'

[75] Inventors: Yasunori Yomo, Yamanashi; Yasuyuki Murakami, Shiga, both of Japan

[73] Assignee: Suntory Limited, Osaka, Japan

[21] Appl. No.: 08/923,399

[22] Filed: Sep. 4, 1997

[30] Foreign Application Priority Data

Sep. 4, 1996 [JP] Japan ..... 9056

[51] Int. Cl.[6] ..... A01H 5/00

[52] U.S. Cl. ..... Plt./308

[58] Field of Search ..... Plt./87, 308

[56] References Cited

U.S. PATENT DOCUMENTS

| | | | |
|---|---|---|---|
| P.P. 1,330 | 12/1954 | Chandler | Plt./87 |
| P.P. 8,995 | 11/1994 | Tachibana et al. | Plt./87 |
| P.P. 9,014 | 12/1994 | Tachibana et al. | Plt./87 |
| P.P. 9,059 | 2/1995 | Tachibana et al. | Plt./87 |
| P.P. 9,085 | 3/1995 | Tachibana et al. | Plt./87 |
| P.P. 9,121 | 4/1995 | Tachibana et al. | Plt./87 |
| P.P. 9,270 | 8/1995 | Archer | Plt./87 |
| P.P. 9,411 | 12/1995 | Tachibana et al. | Plt./87 |
| P.P. 10,311 | 3/1998 | Tachibana | Plt./87 |

OTHER PUBLICATIONS

GTITM UPOVROM Citation for 'Sanmaribisu' as per JP PBR9056), Sep. 4, 1996.

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

Disclosed herein is a Verbena plant which has a broad spreading growth habit and long stems. The plant forms flowers in clusters with a great profusion of blooms. The blooming period is late April to November and flowering duration is long. The entire plant remains in bloom for a considerable period of time. The flower size is large and the petals of the flowers are a vivid red-purple coloration. The plant is highly tolerant to heat, and exhibits a high resistance to pests and diseases, particularly powdery mildew, and a high resistance to rain is exhibited.

2 Drawing Sheets

BACKGROUNG OF THE VARIETY

The present invention relates to a new and distinct variety of *Verbena hybrida* plant obtained from crossing a *Verbena hybrida* named 'Romance Scarlet with Eye' (♀) and a wild type of Verbena plant *Verbena peruviana* (♂) native to Brazil.

The Verbena is a very popular plant and is used for flower bedding and potting in the summer season. There are only a few varieties of the Verbena plant which have a spreading growth habit, much branching, a large number of flowers in a cluster and which have a high resistance to rain, heat, cold, and diseases. Accordingly, this invention was aimed at obtianing a new variety having a spreading growth habit, strong branching, a large number of flowers in a cluster, a flower of large diameter, a high tolerance to heat and cold, and resistance to diseases and pests, and also having vivid red-purple colored petals.

The new variety of Verbena plant according to this invention originated from crossing a *Verbena hybrida* named 'Romance Scarlet with Eye' (non-patented in the United States) (♀) and a wild type of Verbena plant *Verbena peruviana* (♂) native to Brazil.

Initially, 64 seedling were obtained in the autumn of 1994, from crossing 'Romance Scarlet with Eye' as the female parent and a wild type of Verbena plant (*Verbena peruviana f. rosea*) as the pollen parent in May of 1994. From this crossing, 1 seeedling was selected in view of its spreading growth habit and was propagated by cuttings, and then growth as a trial in flower beds and in planters beginning in the spring of 1995. In the autumn of 1995 the botanical characteristics were examined, using the similar varieties 'Sunmarisu' (non-patented in the United States) and 'Derby Scarlet' (non-patented in the United States) for comparison.

As a result, it was concluded that this Verbena is distinguishable from any other variety, whose existence is known to us, and is uniform and stable in its characteristics, then this new variety of *Verbena hybrida* plant was named 'Sunmaribisu'.

In the following description, the color-coding is in accordance with the Horicultural Color Chart of The Royal Horticultural Society, London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

'Romance Scarlet with Eye' was used as the female parent when obtaining this new variety 'Sunmaribisu'. 'Romance Scarlet with Eye' has an erect growth habit and is publicly available.

The pollen parent used in obtaining this new variety 'Sunmaribisu' was a wild type of Verbena native to South Brazil, *Verbena peruviana*. This wild type of verbena plant is presently maintained at the Hakushu Nursery Center of Suntory Ltd., 2913-1 Torihara, Hakushu-cho, Kitakoma-gun, Yamanashi-ken, Japan. The main botanical characteristcs of this pollen parent are as follows when grown at the Hakushu Nursery Center of Suntory ltd., 2913-1 Torihara, Hakushu-cho, Kitakoma-gun, Yamanashi-ken, Japan.

Plant:

*Growth habit.*—Spreading
*Plant height.*—10–20 cm.
*Plant width*—100–150 cm.

Stem:

*Diameter.*—1.0–2.0 mm.
*Anthocyanin pigmentation.*—Present.
*Branching.*—Medium.

*Pubescence*.—Medium.
*Length of internode*.—3.0–4.0 cm.
Leaf:
*Phyllotaxis*.—Opposite.
*Shape of blade*.—Hastate.
*Length*.—3.0–4.0 cm.
*Width*.—1.5–2.0 cm.
*Depth of incision*.—Shallow.
*Color*.—Moderate olive green (R.H.S. 146A, JHS 3509).
*Pubescence*.—Slight.
Flower:
*Facing direction*.—Upward.
*Outward curvature of petal*.—Slightly curved.
*Diameter*.—2.0–3.0 cm.
*Height*.—20–30 mm.
*Color*.—Strong reddish purple (R.H.S. 77B, JHS 8911).
*Color presentation*.—Substantially even.
*Overlapping of petals*.—Opened.
*Flower cluster*.—30–40 mm in length; and 50–60 mm in diameter.
*Calyx*.—1.5–2.0 cm in length.
*Anthocyanin pigmentation of calyx limb*.—Absent.
*Peduncle*.—1–2 mm in thickness, and 3.0–5.0 cm in length.
*Number of flowers*.—Plentiful (approximately 10–14).
*Reproductive organs*.—1 pistil and 4 stamens.
*Flower fragrance*.—Absent.
*Flowering duration*.—Short.
Physiological and ecological characteristics: High resistance to diseases and pests, and high tolerance to heat and cold.

The 'Sunmarisu' variety was used as a comparison for this new 'Sunmaribisu' variety. The main botanical characteristics of the 'Sunmarisu' variety are as follows when grown at the Hakushu Nursery Center of Suntory Ltd., 2913-1 Torihara, Hakushu-cho, Kitakoma-gun Yamanasi-ken Japan.

Plant:
*Growth habit*.—Slightly erect with some spreading.
*Plant height*.—20–30 cm.
*Plant width*.—30–50 cm.
*Growth*.—Very vigorous with abundant branching and great profusion of blooms; with the entire plant remaining in bloom for an extended period of time.
Stem:
*Diameter*.—2.0–3.0 mm.
*Anthocyanin pigmentation*.—Present.
*Branching*.—Abundant.
*Pubescence*.—Medium.
*Length of internode*.—3.0–6.0 cm.
Leaf:
*Phyllotaxis*.—Opposite.
*Shape of blade*.—Hastate.
*Length*.—4.0–6.0 cm.
*Width*.—2.0–3.0 cm.
*Depth of incision*.—Shallow.
*Color*.—Dark olive green (R.H.S. 137B, JHS 3708) *Pubescence*.—Slight.
Flower:
*Facing direction*.—Upward.
*Outward curvature of petal*.—Slightly curved.
*Diameter*.—2.0 cm.
*Height*.—15–20 mm.
*Color*.—Vivid red (R.H.S. 52A, JHS 0407).
*Color presentation*.—Substantially even.
*Overlapping of petals*.—Separate.
*Cluster*.—30–40 mm in length; and 50–70 mm in diameter.
*Calyx*.—1.0–1.5 cm in length.
*Anthocyanin pigmentation of calyx limb*.—Absent.
*Peduncle*.—2–3 mm in thickness; and 4.0–7.0 cm in length.
*Number of flowers*.—Plentiful (approximately 15–20).
*Reproductive organs*.—1 pistil and 5 stamens.
*Flower fragrance*.—Absent.
*Flowering duration*.—Long.
Physiological and ecological characteristics: High resistance to diseases and pests, particularly powdery mildew. High tolerance to heat and moderate tolerance to cold.

The 'Derby Scarlet' variety was used as a comparison for this new 'Sunmaribisu' variety. The main botanical characteristics of the 'Derby Scarlet' variety are as follows when grown at the Hakushu Nursery Center of Suntory Ltd., 2913-1 Torihara, Hakushu-cho, Kitakoma-gun, Yamanashi-ken, Japan.

Plant:
*Growth habit*.—Semi-erect.
*Plant extension*.—Medium.
Stem:
*Anthocyanin pigmentation*.—Absent.
*Branching*.—Slight.
*Pubescence*.—Medium.
*Length of internode*.—Short.
Leaf:
*Phyllotaxis*.—Opposite.
*Length*.—Medium.
*Width*.—Medium.
*Depth of incision*.—Shallow.
*Color*.—Dark green.
*Pubescence*.—Medium.
Flower:
*Facing direction*.—Upward.
*Outward curvature of petal*.—None.
*Diameter*.—Large
*Height*.—Medium.
*Color*.—Deep reddish brown (JHS 0708).
*Color presentation*.—Substantially even.
*Overlapping of petals*.—Closed.
*Cluster*.—Medium in length; and medium in diameter.
*Anthocyanin pigmentation of calyx limb*.—Absent.
*Peduncle*.—Medium in thickness; and medium in length.
*Number of flowers*.—Medium.
*Reprodcutive organs*.—1 pistil and 5 stamens.
*Flower fragrance*.—Absent.
*Flowering duration*.—Medium.
Physiological and ecological characteristics: Weak resistance to diseases, pests, heat and cold.

This new variety of verbena plant 'Sunmaribisu' was asexually reproduced by cuttings at the Hakushu Nursery Center of Suntory Ltd., 2913-1 Torihara, Hakushu-cho, Kitakoma-gun, Yamanashi-ken, Japan, and the homogeneity and stability thereof were confirmed. The characteristics of the new variety are fully stable following such asexual reproduction.

SUMMARY OF THE VARIETY

This new variety of Verbena plant has a broad spreading growth habit and long stems. The plant is well branched and abundantly forms flowers in a cluster. The blooms are present in profusion. The blooming period is late April to November and the flowering duration is long. The entire plant remains in bloom for an extended period of time. The flower size is large and the petal coloration of the flowers is vivid red. The plant is highly tolerant to heat, exhibits a high resistance to pests and diseases, particulary powdery mildew, and a high resistance to rain is exhibited.

Figure 1:
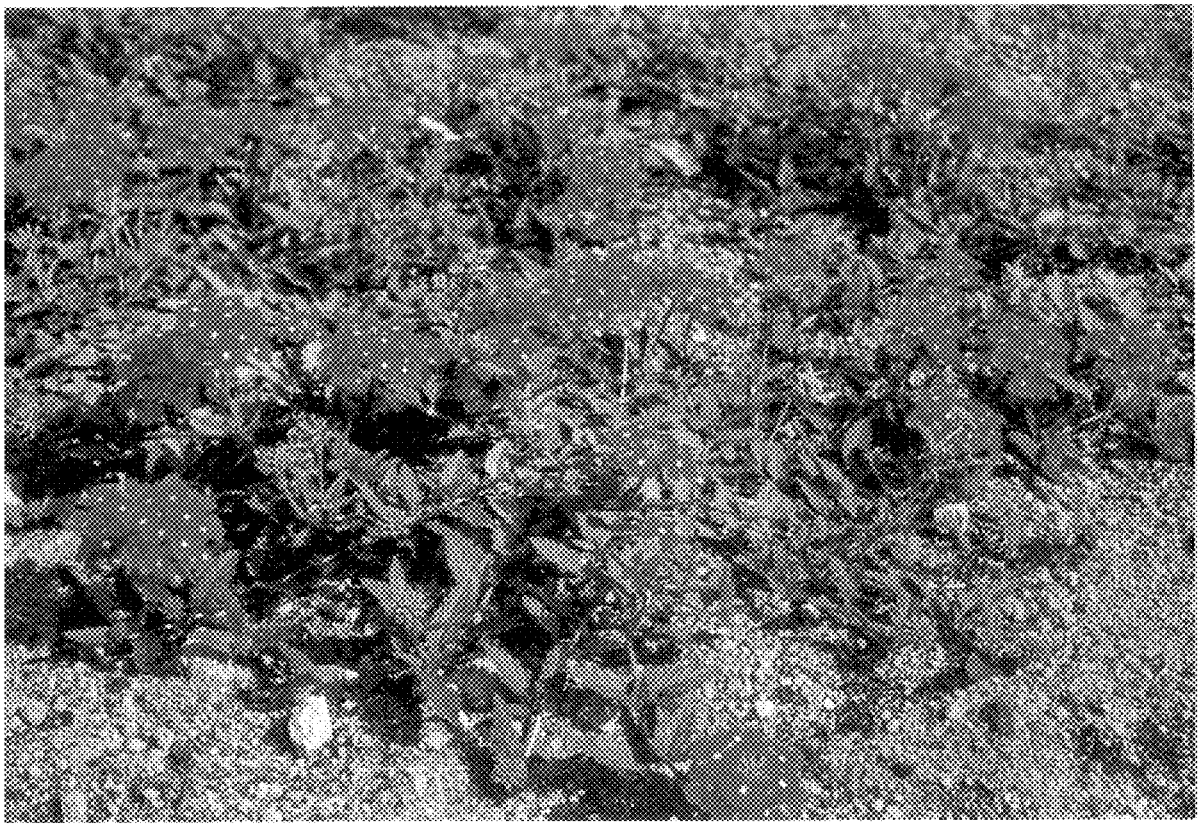
FIG. 1 depicts a side view of the 'Sunmaribisu' plant of the present invention.
Figure 2:
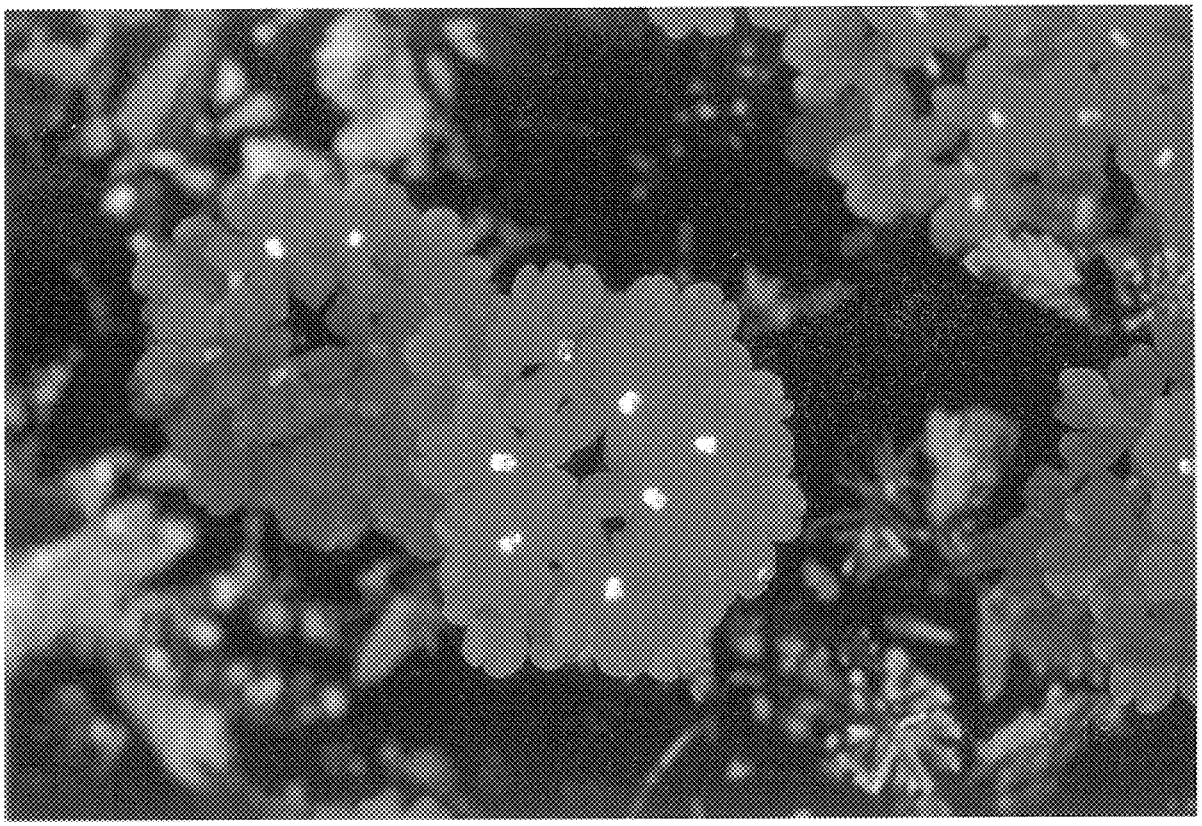
FIG. 2 depicts a close-up view of the flowers of the 'Sunmaribisu' plant of the present invention.

As indicated hereafter, the actual flower coloration is more red-purple than illustrated in the photographs. Accordingly, reference should be made to the color chart information provided hereafter when specifying flower coloration.

DESCRIPTION OF THE VARIETY

The botanical characteristics of the new and distinct variety of Verbena plant, 'Sunmaribisu' are as follows when grown at the Hakushu Nursery Center of Suntory Ltd., 2913-1 Torihara, Hakushu-cho, Kitakoma-gun, Yamanashi-ken, Japan.

Plant:
- *Growth habit*.—Spreading.
- *Plant width*.—Broad; 70–90 cm.
- *Plant height*.—Low to medium; 12–21 cm.

Stem:
- *Diameter*.—Medium; 2.2–3.2 mm.
- *Anthocyanin pigmentation*.—Absent.
- *Pubescence*.—Medium.
- *Branching*.—A moderate level of branching is present. Each single branch commonly produces two additional branches. More specifically, a single branch commonly becomes three branches and those three branches commonly produce nine branches, etc.
- *Color*.—R.H.S. 144A, JHS 3507.
- *Subterranean stem*.—Absent. But when the stems contact the surface of soil, the nodes take root in the ground and the plant growth thereby spreads.
- *Length of internode*.—Medium; 2.3–3.9 cm.

Leaf:
- *Phyllotaxis*.—Opposite.
- *Shape of blade*.—Oblong-lanceolate.
- *Depth of blade incision*.—Shallow.
- *Blade margin*.—Doubly dentate and sometimes partially lobed.
- *Length*.—Medium; 2.4–4.7 cm.
- *Width*.—Medium; 1.0–2.5 cm.
- *Leaf apex*.—Acute.
- *Leaf base*.—Peptiolate.
- *Color*.—Deep yellow green (R.H.S. 143A, JHS 3706) on the upper surface and medium yellow green (R.H.S. 144A and JHS 3513) on the under surface.
- *Pubescence*.—Slight.
- *Petiole*.—Present.
- *Diameter of peptiole*.—Medium; 0.6–1.2 mm.
- *Length of petiole*.—Short; 2.4–4.0 mm.
- *Petiole color*.—R.H.S. 144A, JHS 3507.

Flower:
- *Shape of cluster*.—Obovate.
- *Length of cluster*.—Medium; 22–40 mm.
- *Diameter of cluster*.—Medium to large; 58–68 mm.
- *Facing direction*.—Upward.
- *Outward curvature of petal*.—Slightly curved.
- *Diameter*.—Very large; 2.3–2.4 cm.
- *Height*.—Medium; 1.8–2.0 cm.
- *Color*.—Vivid red-purple (R.H.S. 57A, JHS 0407) on the upper surface and R.H.S. 52A, JHS 0106 on the under surface. The petal coloration fades slightly with age.
- *Eye color*.—Pale yellow (R.H.S. 11D, JHS 2503).
- *Eye size*.—Small.
- *Variegation on petal*.—Absent.
- *Color presentation*.—Substantially even.
- *Overlapping of petals*.—Separate.
- *Incision of petal*.—Present.
- *Number of petals*.—Medium; 5.
- *Sepals*.—Tubular in configuration.
- *Length of calyx*.—Long; 1.1–1.2 cm.
- *Anthocyanin pigmentation of calyx limb*.—Absent.
- *Color of anther*.—Yellow green.
- *Diameter of peduncle*.—Medium; 1.4–1.8 mm.
- *Length of peduncle*.—Medium; 35–70 mm.
- *Color of peduncle*.—Strong yellow green, R.H.S. 144A, JHS 3507.
- *Number of flowers*.—Plentiful; approximately 15±2.
- *Flower bearing*.—In a cluster (as illustrated).
- *Reproductive organs*.—1 pistil and 4 stamens.
- *Flower fragrance*.—Absent.
- *Pollen*.—Brilliant greenish-yellow (R.H.S. 6C, JHS 2704) in coloration.
- *Flowering time*.—Early.
- *Flowering duration*.—Long. When planted during March, the plant commonly blossoms from April to November A bloom cluster commonly is present for approximately 2 to 3 weeks, and an individual bloom within the cluster commonly lasts for approximately 7 to 10 days on the plant.

Physiological and ecological characteristics: High resistance to diseases and pests, particularly powdery mildew. High tolerance to heat and drought. High tolerance to rain. Medium resistance to cold.

This new variety of verbena plant is most suitable for flower bedding and potting, particularly in planters, and is further excellent for use as a ground cover.

We claim:

1. A new and distinct variety of Verbena plant having the following combination of characteristics:

(a) exhibits a broad spreading growth habit with long stems,
(b) forms in abundance clusters of attractive vivid red-purple blossoms that remain on the plant for an extended period of time, and
(c) exhibits good tolerance to rain, heat, drought, and diseases;

substantially as shown and described.

* * * * *